United States Patent [19]

Trigger

[11] Patent Number: 5,594,013
[45] Date of Patent: Jan. 14, 1997

[54] PHARMACEUTICAL COMPOSITIONS CONTAINING NIFEDIPINE AND PROCESS FOR THE PREPARATION THEREOF

[75] Inventor: David Trigger, Norfolk, Great Britain

[73] Assignee: Ethical Pharmaceuticals Limited, Great Britain

[21] Appl. No.: 256,398

[22] PCT Filed: Jan. 12, 1993

[86] PCT No.: PCT/GB93/00055

§ 371 Date: Jul. 11, 1994

§ 102(e) Date: Jul. 11, 1994

[87] PCT Pub. No.: WO93/13773

PCT Pub. Date: Jul. 22, 1993

[30] Foreign Application Priority Data

Jan. 13, 1992 [GB] United Kingdom .................. 9200607

[51] Int. Cl.⁶ .................................................. A61K 31/04
[52] U.S. Cl. ..................... 514/356; 424/468; 424/470; 424/472; 424/471; 424/482; 424/501
[58] Field of Search ....................... 424/468, 470, 424/472, 471, 482, 501; 514/356

[56] References Cited

U.S. PATENT DOCUMENTS

| | | | |
|---|---|---|---|
| 4,673,564 | 6/1987 | Kawota et al. | 424/494 |
| 4,740,365 | 4/1988 | Yukimatsu et al. | 424/435 |
| 4,828,836 | 5/1989 | Elger et al. | 424/419 |
| 4,882,144 | 11/1989 | Hegasy | 424/80 |
| 4,894,235 | 1/1990 | Köhne et al. | 424/452 |
| 4,968,508 | 11/1990 | Oren et al. | 424/468 |
| 4,970,075 | 11/1990 | Oshlack et al. | 424/451 |
| 4,981,683 | 1/1991 | Hegasy | 424/80 |

FOREIGN PATENT DOCUMENTS

| | | |
|---|---|---|
| 1180277 | 1/1988 | Canada . |
| 1253079 | 4/1989 | Canada . |
| 001247 | 4/1979 | European Pat. Off. . |
| 047894 | 3/1982 | European Pat. Off. . |
| 2139892 | 11/1984 | European Pat. Off. . |
| 142561 | 5/1985 | European Pat. Off. . |
| 220076 | 5/1987 | European Pat. Off. . |
| 232155 | 8/1987 | European Pat. Off. . |
| 249587 | 12/1987 | European Pat. Off. . |
| 274176 | 7/1988 | European Pat. Off. . |
| 385582 | 5/1990 | European Pat. Off. . |
| 387782 | 9/1990 | European Pat. Off. . |
| 386967 | 9/1990 | European Pat. Off. . |
| 410422 | 1/1991 | European Pat. Off. . |
| 0167909 | 8/1992 | European Pat. Off. . |
| 1456618 | 11/1976 | United Kingdom . |
| 1579818 | 11/1980 | United Kingdom . |
| 2229095 | 9/1990 | United Kingdom . |
| WO8601717 | 3/1986 | WIPO . |
| WO89102738 | 4/1989 | WIPO . |

OTHER PUBLICATIONS

Sugimoto, I., et al., "Dissolution and absorption of nifedipine from nifedipine–polyvinylpyrroidone coprecipitate", *Drug Development and Industrial Pharmacy*, 6(2):137 (1980).

Sugimoto, I., et al., "Stability and bioavailability in fine granules," *Chem. Pharm. Bull.*, 30:4479 (1982).

*Primary Examiner*—Brian M. Burn
*Attorney, Agent, or Firm*—Flehr, Hohbach, Test, Albritton & Herbert

[57] ABSTRACT

This invention relates to a slow release nifedipine-containing pharmaceutical compositions and methods of making such compositions. The compositions of the inventions comprise a soluble carrier coated with nifedipine and polyvinylpyrrolidone and an acrylic based polymer. Nifedipine is present, in amorphous form, in excess amounts to polyvinylpyrrolidone and in equal or excess amounts to the acrylic based polymer.

17 Claims, 4 Drawing Sheets

Fig.5

PHARMACEUTICAL COMPOSITIONS CONTAINING NIFEDIPINE AND PROCESS FOR THE PREPARATION THEREOF

INTRODUCTION

This introduction is a 371 of PCT/GB93/00055, filed Jan. 12, 1993, and published as WO93/13773 Jul. 22, 1993.

1. Technical Field

The present invention relates to pharmaceutical compositions containing nifedipine and to a process for the preparation thereof. In particular the present invention relates to a slow release pharmaceutical formulation containing nifedipine which provides for a regular and prolonged release pattern upon administration and, in its most preferred form, may be administered once a day. The invention also relates to a process for the preparation thereof.

2. Background to the Invention

The drug nifedipine is currently used in the form of rapid release and comparatively slow release pharmaceutical dosage forms for the treatment, respectively, of acute angina and chronic hypertension. It appears that, for the acute treatment of angina, it is desirable quickly to attain relatively high nifedipine concentrations in plasma and this requirement is currently served by a preparation consisting of a solution of nifedipine in low molecular weight polyethylene glycol contained within soft gelatin capsules. For the treatment of hypertension it appears that it is more desirable to maintain plasma nifedipine concentrations within a much lower concentration range. Modified release preparations of the substance are available for this purpose, although they mostly still require multiple daily doses to be taken which is both a clinical disadvantage in that symptomatic control of the condition may not be optimised and a disadvantage from the patient's point of view. The inconvenience of taking a dosage more than once per day may affect compliance with the dosage regime, also leading to poor clinical performance.

The reason for the two significantly different types of formulation is that nifedipine per se is very poorly soluble in water. Because of this many of the patent specifications on controlled release systems of nifedipine describe means of actually enhancing, rather than suppressing, the solubility of nifedipine.

Thus, in European Patent No. 0047899 (corresponding to Canadian Patent No. 1180277) control of the dissolution of nifedipine is achieved by processing the material to give it a large specific surface area of 0.5 to 6m$^2$/g. The specification discloses the production of fine nifedipine crystals by grinding and screening but not by any other means.

Similarly, in PCT/EP85/00481 the control of nifedipine dissolution is achieved by limiting its specific surface area to 0.1 to 0.42m$^2$/g and coating the nifedipine crystals, in admixture with an equal quantity of a filler, onto inert spheroids by means of suitable binders.

Further enhancement of the dissolution of nifedipine is achieved by processing the material to form a solution adsorbed onto a solid base (as in British Patent No. 1,456,618), or to form a solid solution (also known as a coprecipitate) with high molecular weight polyethylene glycol (European Patent Application No. 0220760) or an ester or ether of polyethylene glycol (European Patent Application No. 0249587) or with other selected materials, including polyvinylpyrrolidone (British Patent No. 1,579,818).

This ability of polyvinylpyrrolidone to enhance the solubility characteristics of certain materials by forming coprecipitates with them is now fairly well documented. It is also generally accepted that in order to form such coprecipitates the amount of polyvinylpyrrolidone used must be in excess of the amount of active material.

In our European Patent No. 385582 we describe pharmaceutical compositions in which polyvinylpyrrolidone in an amount less than the amount of nifedipine actually significantly slows the dissolution of nifedipine from the finished solid dosage form. More specifically, EP 385582 discloses a pharmaceutical composition which comprises particles of a finely divided pharmaceutically acceptable water soluble carrier coated with microparticles of nifedipine, the majority of which have a particle size of 100 micrometers or less, in the presence of polyvinylpyrrolidone, the polyvinylpyrrolidone being present in an amount of from 10 to 90% by weight based on the weight of the nifedipine.

We have found that these compositions can provide a slow release of nifedipine over a period of up to about 12 hours, i.e. to provide a potential composition for twice-daily administration of nifedipine. Attempts to slow the release of nifedipine from the tablets by increasing the amount of polyvinylpyrrolidone were unsuccessful and the addition of other materials to the system diluted the effect of polyvinylpyrrolidone and thus only succeeded in speeding the release of nifedipine from the compositions.

Acrylic resins have previously been used in tablet compositions. However, they have been used in much larger relative amounts than in the present invention, and the resulting compositions have short release profiles.

GB 2229095 describes compositions containing nifedipine in crystalline form, hydrophilising agent and retarding agent. Polyvinylpyrrolidone is mentioned as a hydrophilising agent, but no example is given. For sustained release composition, the amount of retarding agent required is in the range 0.2 to 1.5 parts by weight relative to the nifedipine content. In this document, polyvinyl butyrate is preferred as the retarding agent because a smaller amount is said to be required than if an acrylic polymer is used.

In WO86/01717 nifedipine is coated by spraying onto sucrose granules which have first been wetted with polyvinylpyrrolidone. The coated granules are then wetted with Eudragit (an acrylic polymer) in a ratio of 35 parts by weight Eudragit to one part by weight of nifedipine.

Sugimoto et al. in Drug Development and Industrial Pharmacy (1980), 6, p137–160 and Chem. Pharm. Bull (1982) 30 (12) p4479–2288 discuss the use of polymeric materials to increase the solubility of PVP in co-precipitates, resulting in nifedipine formulations with rapid release characteristics. Where PVP is mentioned, the amount of PVP used in the co-precipitates of nifedipine with PVP is always in amounts in excess of the nifedipine content.

SUMMARY OF THE INVENTION

There is a need for a potential product for once-daily administration of nifedipine. We have surprisingly discovered that the addition of an acrylic resin to certain pharmaceutical compositions, for example those disclosed in our earlier European Patent No. 385582 results in compositions that can become useful as once a day treatments.

The present invention provides a pharmaceutical composition which comprises particles of a finely divided pharmaceutically acceptable water soluble carrier coated with a mixture of nifedipine with polyvinylpyrrolidone or a copolymer of N-vinyl-pyrrolidone and vinyl acetate, and a pharmaceutically acceptable acrylic based polymer, the weight ratio of the polyvinylpyrrolidone or copolymer of N-vinylpyrrolidone and vinyl acetate copolymer to the content of nifedipine being in the range of from 1:1 to 1:10 and the weight ratio of the acrylic based polymer to the content of nifedipine being in the range of from 1:4 to 1:20.

The present invention also includes within its scope a process for the preparation of the pharmaceutical compositions as defined above, which process comprises forming a solution of nifedipine, polyvinylpyrrolidone or a copolymer of N-vinylpyrrolidone and vinyl acetate and a pharmaceutically acceptable acrylic based polymer (which may for example be an acrylic resin) in a suitable solvent, coating particles of a finely divided pharmaceutically acceptable water soluble carrier which is insoluble in the solvent with the solution and evaporating the solvent from the surface of the coated carrier particles.

Throughout the present specification the copolymer of N-vinylpyrrolidone and vinyl acetate will be referred to as an "N-vinylpyrrolidone copolymer". A suitable example of such a copolymer is Kollidon VA 64 obtainable from BASF.

All ratios are by weight. Preferably, the ratio of the acrylic based polymer to the content of nifedipine is in the range 1:5 to 1:12. Most preferably this ratio is in the range 1:6 to 1:10.

It is further preferable that the ratio of the content of polyvinylpyrrolidone or N-vinylpyrrolidone copolymer in the composition to the content of nifedipine is in the range 1:2 to 1:8. Very preferably this ratio is in the range 1:2 to 1:5. A particularly advantageous ratio is 1:4.

In a highly preferred form of the invention the nifedipine is present in a predominantly amorphous form in the composition. We believe that the composition is a highly amorphous layer of a solid solution of polyvinylpyrrolidone (or N-vinylpyrrolidone copolymer), nifedipine and acrylic based polymer coated on the carrier, as distinct from the nifedipine being in crystalline form. However, the invention is not be be limited by theoretical considerations and the possibility is not excluded that some of the nifedipine may have some crystalline structure.

In our own SEM (scanning electron microscope) studies, no crystalline nifedipine was seen.

Preferably the amount of drug released from a composition according to the invention in an in vitro dissolution test is related to time by a linear relationship better than by a square-root of time relationship.

Advantageously, dosage units formed from a composition of the invention can provide substantially linear release of nifedipine over 8 hours, or more.

DESCRIPTION OF SPECIFIC EMODIMENTS

The pharmaceutically acceptable water soluble carrier may be any carrier which is normally used in the preparation of pharmaceutical compositions, for example lactose, sucrose, mannose, sorbitol, or mixtures thereof. The pharmaceutically acceptable water soluble carrier preferably has a particle size of less than 250 micrometers and preferably also has a specific surface area of greater than 0.5 $m^2$/gram.

Although polyvinylpyrrolidone and N-vinylpyrrolidone copolymer are known as binders for use in the preparation of various pharmaceutical compositions, these materials have, when used in the proportions herein specified and incorporated together with the acrylic based polymer in the manner described, a specific effect in controlling the rate of dissolution and release of nifedipine from the coated carrier particles.

The pharmaceutically acceptable acrylic based polymer which is incorporated into the pharmaceutical compositions of the present invention may be any suitable pharmaceutically acceptable acrylic based polymer. By acrylic based polymer we mean a polymer whose monomer units are primarily or entirely acrylic or allylacrylate. Low amounts e.g. up to 10% by weight of co-monomer may be present. The acrylic based polymer may be cationic, non-ionic or anionic and may be, for example, a poly-acrylate, a polymethacrylate or a copolymer of acrylic and methacrylic acid esters. Any of these may have a low content of quaternary ammonium groups. Non-ionic acrylic based polymers are highly preferred, as are acrylic resins. Examples of suitable acrylic based polymers are the whole of the range sold under the trade name EUDRAGIT BY Rohm Pharma GmbH.

In carrying out the process of the present invention, the water soluble carrier may be coated with the nifedipine/polyvinylpyrrolidone/acrylic based polymer in a single stage process or in a stepwise manner. For example, all of the solution may be coated onto the carrier in one stage or, alternatively and preferably, part of the solution may be coated onto the carrier and the mixture granulated and dried, followed by coating of the dry granulate with the remaining part of the solution and drying and granulating the resulting mixture. This stepwise process may be performed in more than two steps.

The solvent which is used in the process of the invention must be a solvent for nifedipine, the polyvinylpyrrolidone and the acrylic based polymer, but should not dissolve the pharmaceutically acceptable carrier. Examples of suitable solvents are lower aliphatic alcohols, methylene chloride or chloroform. The most preferred solvent for use is chloroform.

The solvent evaporates from the surface of the coated carrier particles thus leaving nifedipine in the presence of the polyvinylpyrrolidone and the acrylic based polymer, coated onto the particles of the finely divided pharmaceutically acceptable water soluble carrier. As mentioned, it is preferred that in this coating the nifedipine shows amorphous, rather than crystalline, characteristics.

The pharmaceutical composition of the present invention may be formulated into a solid unit dosage form, such as tablets or capsules, in a conventional manner. In the preparation of such formulations conventional additives may be used such as lubricants, binders, stabilizers etc.

The pharmaceutical compositions of the present invention possess good stability and are easily reproducible. During the preparation of the compositions milling is not required and this avoids the formation of nifedipine dust.

It will be appreciated that dry milling techniques are tedious and expensive and, furthermore, that the dust from a drug such as nifedipine is potentially hazardous. The process of the present invention thus provides an economic and simple route to the production of a pharmaceutical composition comprising nifedipine.

The present invention will be further described with reference to the following Examples and the accompanying drawings, in which.

BRIEF DESCRIPTION OF THE DRAWINGS

EXPERIMENTAL

A. General Processing Method

Nifedipine and polyvinylpyrrolidone (PVP) were dissolved in chloroform (nominal quantity of 0.15 ml chloroform per tablet containing a nominal content of 30 mg nifedipine) and mixed using a propeller mixer. Acrylic resin (Eudragit RS 100) was dissolved in the resulting solution and mixed for ten minutes.

Lactose was placed in a mixer granulator and granulated with half of the nifedipine/acrylic resin solution. Mixing was continued for one minute after the addition of the solution at which time the mixer was stopped, the bowl scraped down, the mixer re-started and the wet granulate mixed for a further four minutes. The resulting wet granulate was fluid bed dried for fifteen minutes at an air inlet temperature of 60° C.

Dry first-stage granulate was returned to the mixer/granulator and regranulated with the remaining nifedipine/acrylic resin solution and the resulting granulate mixed for one minute. The mixer was stopped, the sides of the bowl scraped down, the mixer re-started and the wet granulate mixed for a further four minutes. The resulting wet granulate was fluid bed dried for ten minutes at an air inlet temperature of 60° C.

The resulting dry granulate was screened through a 1 mm aperture stainless steel sieve and fluid bed dried at an air inlet temperature of 60° C.

Appropriate amounts of hydrogenated castor oil and purified talc to be employed as lubricant were added to the dry granulate and blended in a Y-cone blender for ten minutes.

The resulting lubricated granulate was compressed into tablets.

EXAMPLE 1

Preparation of composition containing acrylic polymer and nifedipine in a weight ratio of 1:12

Using the general procedure detailed in A above tablets were prepared each having the following composition:

|  | Parts by Weight |
| --- | --- |
| Nifedipine | 30.0 |
| Polyvinylpyrrolidone | 7.5 |
| Lactose | 300.0 |
| Acrylic Polymer (Eudragit RS) | 2.5 |
| Hydrogenated Castor Oil | 3.5 |
| Purified Talc | 7.1 |

In vitro dissolution tests were carried out using the USP Dissolution Test Apparatus 2, employing a paddle speed of 50 rpm, operated at 37° C. with 2.5% w/v aqueous sodium dodecylsulphate solution used as the dissolution test medium.

Figure 1:
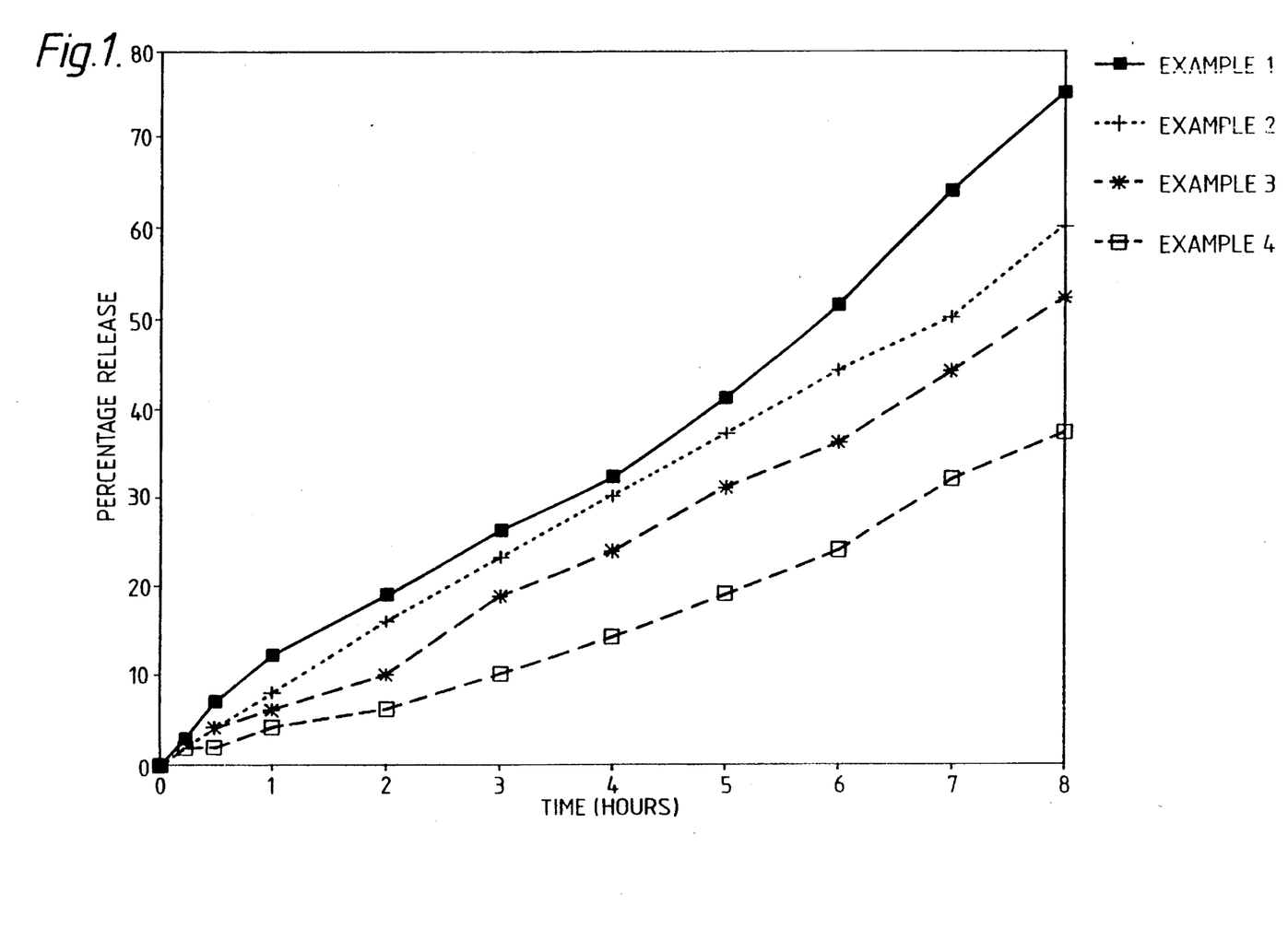
FIG. 1 illustrates the rate of release of nifedipine in in vitro dissolution tests from the tablets of Examples 1 to 4.

The rate of release of nifedipine from these tablets in these dissolution tests is plotted in FIG. 1.

EXAMPLE 2

Preparation of composition containing acrylic polymer and nifedipine in a weight ratio of 1:8.57

Using the general procedure detailed above in A tablets were prepared each having the following composition:

|  | Parts by Weight |
| --- | --- |
| Nifedipine | 30.0 |
| Polyvinylpyrrolidone | 7.5 |
| Lactose | 300.0 |
| Acrylic Polymer (Eudragit RS) | 3.5 |
| Hydrogenated Castor Oil | 3.5 |
| Purified Talc | 7.1 |

Dissolution tests were carried out according to the procedure of Example 1 and the results are plotted in FIG. 1.

EXAMPLE 3

Preparation of composition containing acrylic polymer and nifedipine in a weight ratio of 1:6.67

Using the general procedure detailed above in A tablets were prepared each having the following composition:

|  | Parts by Weight |
| --- | --- |
| Nifedipine | 30.0 |
| Polyvinylpyrrolidone | 7.5 |
| Lactose | 300.0 |
| Acrylic Polymer (Eudragit RS) | 4.5 |
| Hydrogenated Castor Oil | 3.5 |
| Purified Talc | 7.1 |

Dissolution tests were carried out according to the procedure of Example 1B and the results are plotted in FIG. 1.

EXAMPLE 4

Preparation of composition containing acrylic polymer and nifedipine in a weight ratio of 1:4.7

Using the general procedure detailed above in A tablets were prepared each having the following composition:

|  | Parts by Weight |
| --- | --- |
| Nifedipine | 30.0 |
| Polyvinylpyrrolidone | 7.5 |
| Lactose | 300.0 |
| Acrylic Polymer (Eudragit RS) | 6.38 |
| Hydrogenated Castor Oil | 3.5 |
| Purified Talc | 7.1 |

Dissolution tests were carried out according to the procedure of Example 1 and the results are plotted in FIG. 1.

Table 1 presents the dissolution test data of examples 1 to 4 in table form, and shows the dissolution profile over a slightly longer period than does FIG. 1. The table also gives the time to 50% release ($T_{50}$) for each formulation. The $T_{50}$ values of these compositions show that they are useful once-a-day preparations. In particular the formulations of Examples 2 and 3 with $T_{50}$ values of around 7 hours are very useful.

EXAMPLE 5

Preparation of composition containing acrylic polymer and nifedipine in a weight ratio of 1:7.5

Using the general procedure detailed above tablets were prepared each having the following composition:

|  | Parts by Weight |
|---|---|
| Nifedipine | 30.0 |
| Polyvinylpyrrolidone | 7.5 |
| Lactose | 300.0 |
| Acrylic Polymer (Eudragit RS) | 4.0 |
| Hydrogenated Castor Oil | 3.5 |
| Purified Talc | 7.1 |

Tablets of this Example were used in a test described below.

TABLE 1

Dissolution test profile:
mean percentage released from 6 replicate tables at time (hour)

| Time (h) | Example 1 | Example 2 | Example 3 | Example 4 |
|---|---|---|---|---|
| 1.0 |  |  |  |  |
| 1.5 | 16 | 10 |  |  |
| 2.0 |  |  | 7 | 4 |
| 3.0 | 31 | 18 | 15 | 6 |
| 4.0 |  |  | 22 | 10 |
| 4.5 | 48 | 29 | 28 | 14 |
| 5.0 |  |  | 35 | 19 |
| 6.0 | 70 | 42 | 45 | 24 |
| 7.0 |  |  | 52 | 32 |
| 7.5 | 84 | 57 |  |  |
| 8.0 |  |  | 62 | 37 |
| 9.0 |  | 73 |  |  |
| 10.0 |  |  | 77 |  |
| 10.5 |  | 85 |  |  |
| 12.0 |  |  | 86 |  |
| 16.0 |  |  |  | 80 |
| 17.0 |  |  |  | 85 |
| $T_{50}$** | 4.6 | 6.8 | 6.8 | 11.4 |

**$T_{50}$ = Time to 50% release

The in vitro dissolution procedure used in these tests has been shown to give results that correlate very satisfactorily with in vivo results over a wide range of release rates.

EXAMPLE 6

Table 2 below shows the results of in vitro dissolution tests carried out as in Examples 1–4 on three development scale batches with polyvinylpyrolidone and nifedipine in weight ratios of 1:7.9, 1:4 and 1:2.7. The acrylic polymer (Eudragit RS) in each batch formulation was in a weight ratio of 1:6.67 with respect to nifedipine. Batch No. 2 was equivalent to the formulation in Example 3.

| Batch No. | 1 | 2 | 3 |
|---|---|---|---|
| PVP:N ratio | 1:7.9 | 1:4 | 1:2.7 |
| time (h) | % nifedipine released | | |
| 0.25 | 2 | 2 | 1 |
| 0.5 | 3 | 4 | 4 |
| 1 | 8 | 7 | 5 |
| 2 | 13 | 13 | 11 |
| 3 | 21 | 21 | 16 |
| 4 | 30 | 26 | 22 |
| 5 | 36 | 33 | 26 |
| 6 | 42 | 40 | 29 |
| 7 | 49 | 48 | 33 |
| 8 | 55 | 57 | 39 |

RELEASE CHARACTERISTICS

We found that the profile of drug release from compositions according to the present invention closely follows zero-order kinetics. This is in contrast to the prior art products for which the profile is non-linear due to diffusion controlled release of drug. The linear release profile has a significant advantage because a steady rate of supply of drug to the body will result in relatively steady blood levels. In the treatment of chronic heart conditions with nifedipine this is especially advantageous. Furthermore, the side-effects associated with The use of nifedipine may be reduced since these are often associated with peaks in the level of nifedipine in the blood.

Statistical analyses of release data from batches of tablets subjected to the in vitro dissolution rest show that the pattern of drug release from tablets according to the present invention follows substantially zero-order release kinetics. In other words, the relationship between the amount of drug released and time is linear. This means that the amount of drug available for absorption is fairly constant over a period of time.

The release data from individual replicate tablets is modelled according to the equations representing:

(a) the linear relationship of the amount of drug released (Q) as a function of time (t) in the in vitro dissolution test (Q∝t) and (b) the relationship between the amount of drug released (Q) and the square root of time ($\sqrt{t}$) in the in vitro dissolution test (Q∝$\sqrt{t}$) from start up to a level of at least 70% release from the product in each case.

1. The relative goodness of fit of the experimental results to each of the models is assessed by Pearson's product moment correlation coefficient (r value) for each individual tablet tested.

2. Each r value is transformed to 'Fisher's Z' value by calculation as follows:

$$Z = 0.5 \ln \frac{1+r}{1-r}$$

3. The replicate values of 'Z' obtained from the individual tablet dissolution results from the linear and square-root of time relationships are then compared using standard parametric statistical procedures, for example, two sample t tests or the one-way analysis of variance (ANOVA) test to determine the statistical significance of the difference of the goodness of fit of the experimental data to each of these relationships.

By a linear relationship we mean a relationship in which either or both of the following conditions is satisfied:

a) the arithmetic mean value of Z from replicate drug release results fitted to the linear relationship is greater than the arithmetic mean value of Z from the replicate drug release results fitted to the square-root of time relationship and/or b) in the t test (or ANOVA) the significance of the difference (one-tailed) is equal to, or less than, a value of p=0.5.

Such a p value represents the situation where there is at least 95% probability that the fit of the experimental release results to the linear model is better than that to the square-root of time model.

The results of the statistical analysis on batch data is tabulated below (Table 3). The batches represent a formulation series containing Eudragit (as the acrylic based polymer) over a range. They also represent development-scale (3300 tablets) up to production-scale (113000 tablets) manufacture: in each case, the results indicate that the goodness of fit of the in vitro release data to the zero-order model is better than to the square-root of time relationship.

TABLE 3

|  | Example 1 | Example 2 | Example 5 | Example 3 | Example 3 | Example 3 | Example 4 |
| --- | --- | --- | --- | --- | --- | --- | --- |
| Batch size (number of tablets) | 3300 | 113000 | 113000 | 3300 | 3300 | 56800 | 3300 |
| Content of nifedipine (mg/tablet) | 30 | 30 | 30 | 30 | 30 | 30 | 30 |
| Content of acrylic resin (mg/tablet) | 2.5 | 3.5 | 4.0 | 4.5 | 4.5 | 4.5 | 6.4 |
| Fit to zero-order relationship: | | | | | | | |
| r = | 0.9973 | 0.9970 | 0.9968 | 0.9967 | 0.9921 | 0.9990 | 0.9960 |
| Z = | 3.2984 | 3.2553 | 3.2176 | 3.2030 | 2.7673 | 3.8107 | 3.1032 |
| Fit to square-root of time relationship: | | | | | | | |
| r = | 0.9885 | 0.9810 | 0.9893 | 0.9729 | 0.9617 | 0.9889 | 0.9464 |
| Z = | 2.5779 | 2.3222 | 2.6126 | 2.1440 | 1.9678 | 2.5958 | 1.7958 |
| Ratio $\frac{Z_{zero-order}}{Z_{\sqrt{time}}}$ | 1.28 | 1.40 | 1.23 | 1.49 | 1.41 | 1.47 | 1.73 |
| Significance of difference between Z zero order/Z sq rt time: p = | <0.001 | <0.001 | 0.013 | <0.001 | <0.001 | <0.001 | <0.001 |

The findings show that it is possible to obtain zero-order drug release from the tablets a) over a range of formulations and b) when producing the tablets either in the laboratory (development-scale batches) or on conventional pharmaceutical production-scale processing plant.

EXAMPLE 7

Figure 2:
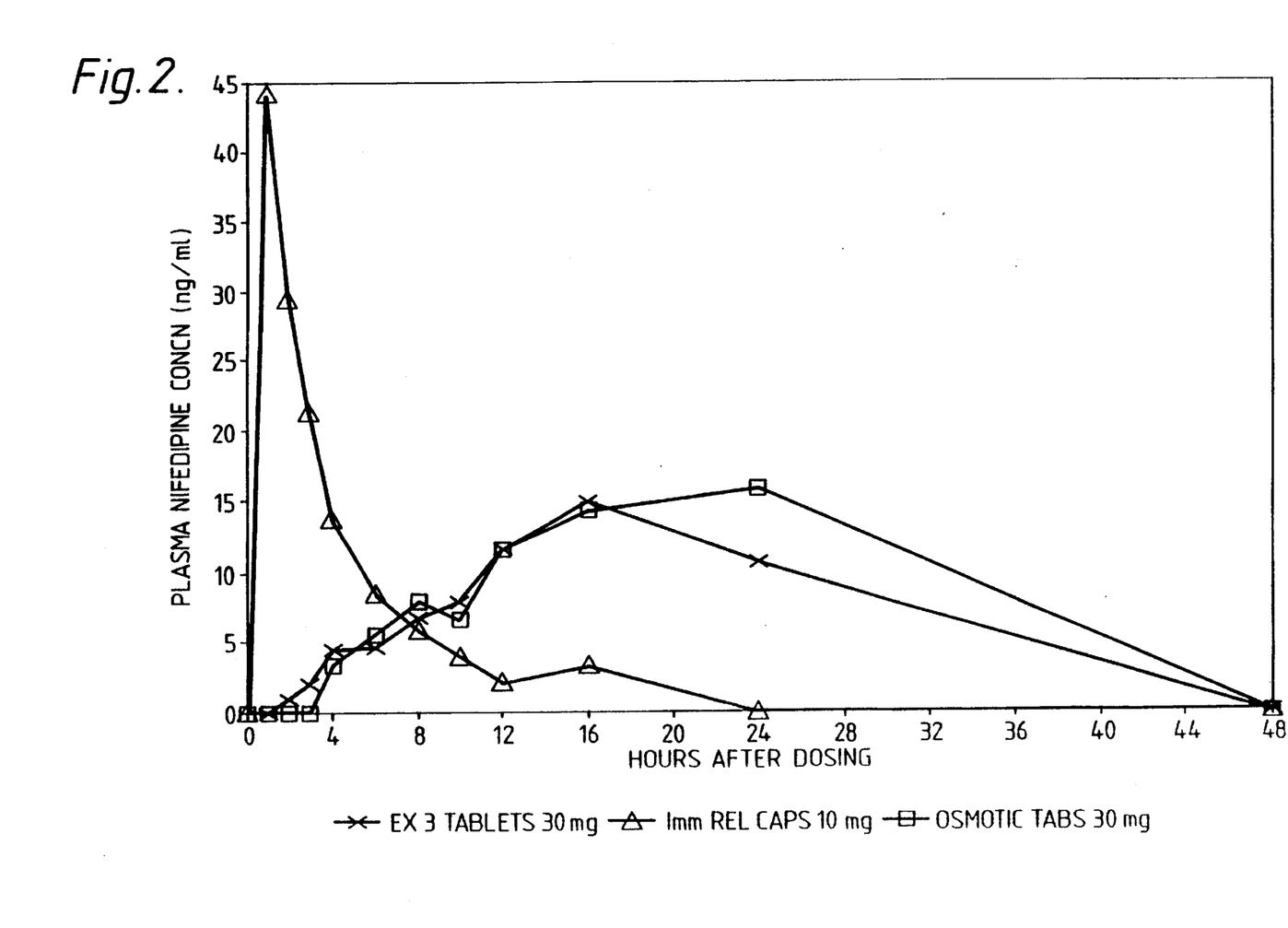
FIG. 2 illustrates mean blood levels of nifedipine attained after administration to human volunteers of one tablet as described in Example 3 in comparison with two other compositions.

FIG. 2 illustrates the levels of intact nifedipine, i.e. the drug that has nor undergone any form of metabolism and which is present in the blood circulation in the chemical form in which it has been administered, following single doses of 10 mg of an immediately-releasing formulation (labelled as Imm rel caps), or 30 mg in the form of the tablets of Example 3, or in the form of Procardia XL tablets which is a controlled-release nifedipine product marketed in the USA as an osmotically regulated device (labelled as osmotic tab 30 mg).

The blood level vs time profile for the product of Example 3 shows the following advantages:

i) it shows a prolongation of nifedipine release and absorption into the body compared with the immediately releasing product;

ii) it does not suffer from the initial lag-time shown by the product which is in the form of an osmotically regulated device, and iii) it can provide for controlled release of the nifedipine in a manner which suggests the clinical usefulness of the product when administered once daily.

EXAMPLE 8

Three sets of granules were manufactured according to (a) Example 2 in a small batch of 3,000 tablets (set 1), (b) Example 2 in a batch of 113,000 tablets (set 2) and (c) Example 3 (except for the drying step) in a batch of 3,300 tablets (set 3). The sets were used in a scanning electron microscopic study. The granules in set 3 were tray dried instead of being fluid bed dried.

The granules were mounted and examined using an ISI 100A scanning electron microscope with an accelerating voltage of 10 kv at a working distance of 20 mm.

Figure 3:
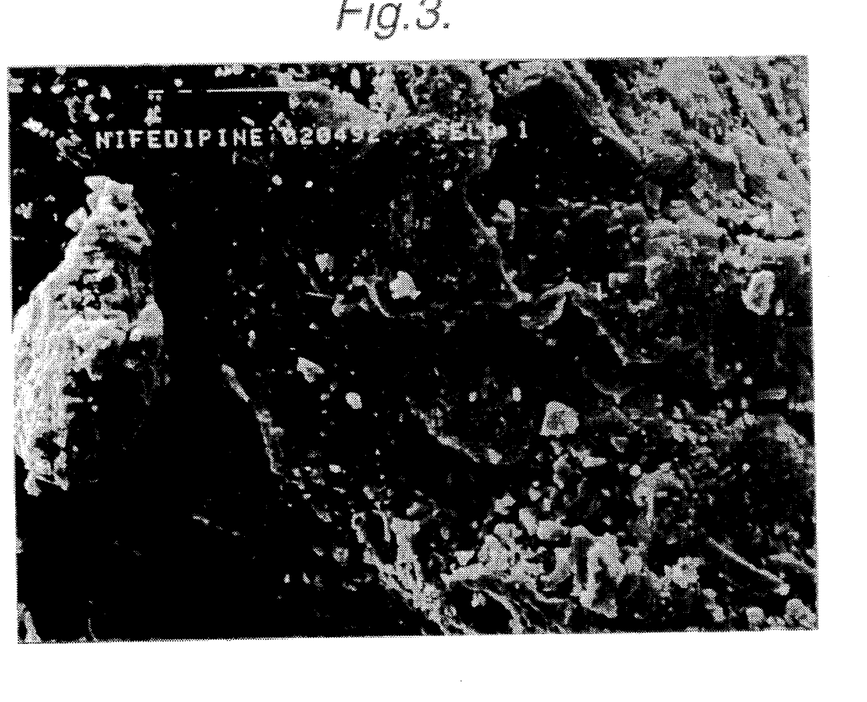
FIGS. 3 to 5 are SEM photomicrographs of granules according To The invention.
Figure 4:
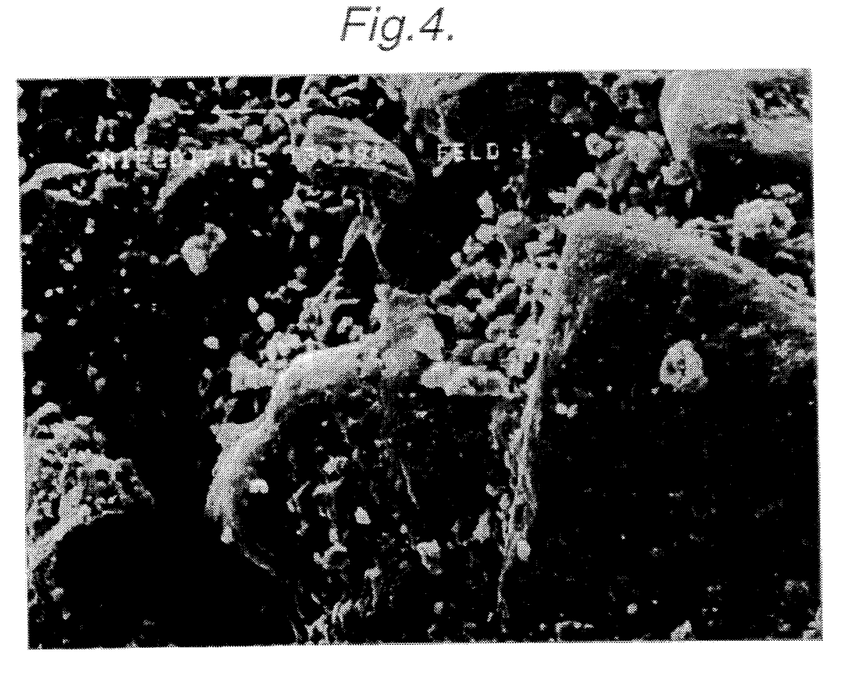
Figure 5:
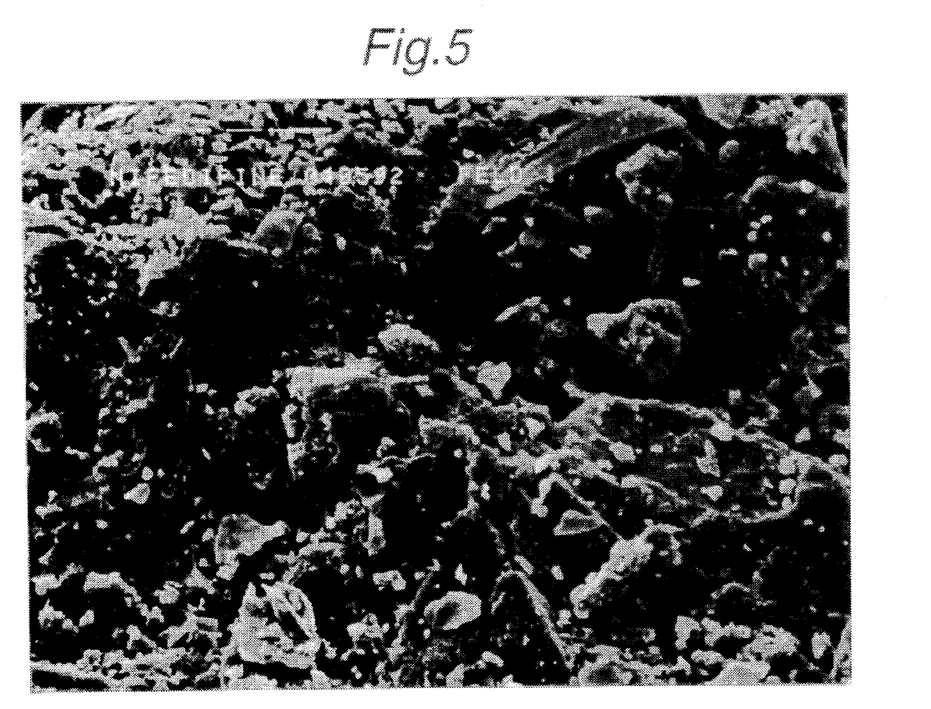

Three fields for each sample were examined at a magnification of ×1250. The results of the magnification in field 1 only are shown in the photomicrographs of FIGS. 3 to 5 (FIG. 3=set 1, FIG. 4=set 2, FIG. 5=set 3). The other two fields gave a similar appearance. All three sets gave the appearance of standard tablet granules. No nifedipine crystals were seen in any of the fields of view indicating that nifedipine is present in a amorphous phase.

I claim:

1. A slow-release pharmaceutical composition which comprises particles of a finely divided pharmaceutically acceptable water soluble carrier coated with a solid solution containing a mixture of nifedipine, polyvinylpyrrolidone or a copolymer of N-vinylpyrrolidone and vinyl acetate, and a pharmaceutically acceptable acrylic based polymer, the weight ratio of the polyvinylpyrrolidone or copolymer of N-vinyl-pyrrolidone and vinyl acetate to the content of nifedipine being in a range of from 1:1 to 1:10 and the weight ratio of the acrylic based polymer to the content of nifedipine being in the range of from 1:4 to 1:20.

2. A composition according to claim 1 wherein said ratio of the acrylic based polymer to the content of nifedipine is in the range 1:5 to 1:12.

3. A composition according to claim 1 wherein said ratio of the acrylic based polymer to the content of nifedipine in the composition is in the range 1:6 to 1:10.

4. A composition according to claim 1 wherein said ratio of the content of the polyvinylpyrrolidone or copolymer of N-vinyl-pyrrolidone and vinyl acetate to the content of nifedipine in the composition is in the range 1:2 to 1:8.

5. A composition according to claim 4 wherein said ratio of the polyvinylpyrrolidone or copolymer of N-vinylpyrrolidone and vinylacetate is in the range 1:2 to 1:5.

6. A composition according to claim 1 wherein the nifedipine is present in amorphous form.

7. A composition according to claim 1 wherein the pharmaceutically acceptable water soluble carrier has a particle size of less than 250 μm.

8. A composition according to claim 1 wherein the pharmaceutically acceptable water soluble carrier is lactose, sucrose or mannose or a mixture of two or more thereof.

9. A composition according to claim 1 wherein the pharmaceutically acceptable carrier has a surface area of greater than 0.5 $m^2/g$.

10. A composition according to claim 1 which is in the form of a solid unit dosage form.

11. A composition according to claim 10 wherein the solid unit dosage form is a tablet or a capsule.

12. A process for the preparation of a pharmaceutical composition which contains nifedipine as the active agent, polyvinylpyrrolidone or a copolymer of N-vinyl pyrrolidone and vinyl acetate, and a pharmaceutically acceptable acrylic based polymer, the weight ratio of the polyvinylpyrrolidone or copolymer of N-vinyl-pyrrolidone and vinylacetate to the content of nifedipine being in the range of from 1:1 to 1:10 and the weight ratio of the acrylic based polymer to the content of nifedipine being in the range of from 1:4 to 1:20, which process comprises dissolving nifedipine, polyvinylpyrrolidone or the copolymer of N-vinylpyrrolidone and vinyl acetate, and the pharmaceutically acceptable acrylic based polymer in a suitable solvent to form a solution, coating particles of a finely divided pharmaceutically acceptable water soluble carrier which is insoluble in the solvent with said solution and evaporating the solvent from the coated carrier particles.

13. A process according to claim 12 wherein the water soluble carrier is coated with said solution in stepwise fashion.

14. A process according to claim 12 wherein the solvent is a lower aliphatic alcohol, methylene chloride or chloroform.

15. A process according to any one of claim 12 wherein the weight ratio of the polyvinylpyrrolidone or copolymer of N-vinylpyrrolidone and vinyl acetate to the content of nifedipine is from 1:2 to 1:5.

16. A process according to claim 12 wherein the coated particles are formed into a solid unit dosage form.

17. A slow-release pharmaceutical composition which comprises particles of a finely divided pharmaceutically acceptable water soluble carrier coated with a mixture of nifedipine in predominantly amorphous form with polyvinylpyrrolidone or a copolymer of N-vinylpyrrolidone and vinyl acetate, and a pharmaceutically acceptable acrylic based polymer, the weight ratio of the polyvinyl-pyrrolidone or copolymer of N-vinylpyrrolidone and vinyl acetate to the content of nifedipine being in the range of from 1: 1 to 1:10 and the weight ratio of the acrylic based polymer to the content of nifedipine being in the range of from 1:4 to 1:20.

* * * * *